United States Patent [19]

Hartwell et al.

[11] Patent Number: 5,410,087

[45] Date of Patent: * Apr. 25, 1995

[54] CATALYTIC REFORMING OF ALKYLENEAMINES

[75] Inventors: George E. Hartwell; David C. Molzahn; Robert G. Bowman, all of Midland, Mich.

[73] Assignee: The Dow Chemical Company, Midland, Mich.

[*] Notice: The portion of the term of this patent subsequent to Oct. 26, 2010 has been disclaimed.

[21] Appl. No.: 54,195

[22] Filed: Nov. 17, 1993

Related U.S. Application Data

[60] Division of Ser. No. 932,410, Aug. 19, 1992, Pat. No. 5,288,909, which is a division of Ser. No. 730,415, Jul. 16, 1991, Pat. No. 5,166,442, which is a continuation-in-part of Ser. No. 611,244, Nov. 9, 1990, Pat. No. 5,118,850, which is a division of Ser. No. 287,189, Dec. 20, 1988, Pat. No. 4,996,363.

[51] Int. Cl.$^6$ .............. C07C 209/00; C07C 209/64; C07D 295/023; C07D 295/13
[52] U.S. Cl. .................... 564/470; 544/401; 544/402; 544/410; 564/346; 564/367; 564/368; 564/369; 564/370; 564/371; 564/503; 564/504; 564/511; 564/512
[58] Field of Search .............. 564/470, 480, 511, 512; 544/358, 401, 402, 410; 502/305, 311, 312

[56] References Cited

U.S. PATENT DOCUMENTS

| | | | |
|---|---|---|---|
| 2,414,552 | 1/1947 | Pfann et al. | 260/250 |
| 2,454,404 | 11/1948 | Pfann et al. | 260/268 |
| 3,297,700 | 1/1967 | Muhlbauer et al. | 260/268 |
| 3,956,329 | 5/1976 | Murakami et al. | 260/268 SY |
| 3,972,939 | 8/1976 | Spielberger et al. | 260/583 P |
| 4,206,150 | 6/1980 | Slaugh | 260/583 R |
| 4,316,840 | 2/1982 | Ford et al. | 260/239 BC |

(List continued on next page.)

FOREIGN PATENT DOCUMENTS

| | | |
|---|---|---|
| 0256516 | 2/1988 | European Pat. Off. |
| 2719718 | 11/1978 | Germany . |
| 2736759 | 3/1979 | Germany . |
| 223706 | 6/1985 | Germany . |
| 2147896 | 5/1985 | United Kingdom . |

OTHER PUBLICATIONS

Anderson et al., "Vapor Phase Contact Deamination, etc" Doklady Akademii Nauk SSS R 1966 vol. 169 No. 6 Khimiya.
Doklady Akademii Nauk SSSR, 169(6), 1332–4(1966).
Latvijas PSR Zinatnum Akademijas Vestis, Kimiijas Serije, 1971(1), 47–58.
U.S. T945-004(Derwent 29753X/16).
Chemical Abstract 84:164140f(1976).
Chemical Abstract 69:67422g (1968).
Chemical Abstract 32:5414$^9$ (1932).
Chemical Abstract 101:229978b (1984).
Chemical Abstract 82:156378h (1975).
Chemical Abstract 66:28327y (1967).
Piperazin. Akad. Nauk Latv. SSR, Inst. Org. Sin. 1965, 41–54.
Chemical Abstract 66:28235w (1967).
Khimiya Geterotsiklicheskikh Soedinenii 1967(2), 346–59.
Derwent 86–163138/26(1984).
Chemical Abstract 73:109263w (1970).

Primary Examiner—Peter O'Sullivan
Attorney, Agent, or Firm—Marie F. Zuckerman

[57] ABSTRACT

A process of reforming an alkyleneamine feedstock or a mixture of such feedstocks to an alkyleneamine or a mixture of alkyleneamines which is different from the feedstock or feedstock mixture. The process is catalyzed by one of the following: Group VB metal oxides, Group VB metal phosphates, Group IIA metal silicates, and tungsten oxides. For example, ethylenediamine is contacted with a catalyst of niobic acid or magnesium silicate to yield predominantly diethylenetriamine and non-cyclic triethylenetetramines; whereas high molecular weight polyethylenepolyamines are cracked by the same catalysts to mixtures of lower molecular weight linear and cyclic materials.

24 Claims, No Drawings

U.S. PATENT DOCUMENTS

| | | | |
|---|---|---|---|
| 4,316,841 | 2/1982 | Ford et al. | 260/239 BC |
| 4,495,369 | 1/1985 | Werner et al. | 564/480 |
| 4,524,143 | 6/1985 | Vanderpool | 502/208 |
| 4,547,591 | 10/1985 | Brennan et al. | 564/479 |
| 4,562,291 | 12/1985 | Wilson, Jr. et al. | 564/463 |
| 4,568,746 | 2/1986 | Cowherd, III | 544/358 |
| 4,605,770 | 8/1986 | Ford et al. | 564/479 |
| 4,625,030 | 11/1986 | Best | 544/358 |
| 4,736,030 | 4/1988 | Mueller et al. | 544/374 |
| 4,906,782 | 3/1990 | Hara et al. | 564/478 |
| 4,927,931 | 5/1990 | Molzahn et al. | 544/357 |
| 4,973,569 | 11/1990 | Bowman et al. | 502/209 |
| 4,982,003 | 1/1991 | Hara et al. | 564/480 |
| 5,256,786 | 10/1993 | Bowman et al. | 564/470 |

CATALYTIC REFORMING OF ALKYLENEAMINES

CROSS-REFERENCE TO RELATED APPLICATION

This is a divisional of application Ser. No. 07/932,410 filed Aug. 19, 1992, now U.S. Pat. No. 5,288,909, which is a divisional of application Ser. No 07/730,415, filed Jul. 16, 1991, now U.S. Pat. No.5,166,442, which is a continuation-in-part of application Ser. No. 07/611,244, filed Nov. 9, 1990, now U.S. Pat. No. 5,118,850, which is a divisional of application Ser. No, 07/287,189, filed Dec. 20, 1988, now U.S. Pat. No. 4,996,363.

BACKGROUND OF THE INVENTION

This invention relates to a catalytic process of reforming an alkyleneamine feedstock, such as diethylenetriamine or higher molecular weight polyethylenepolyamines, to an alkyleneamine product or mixture thereof which is different from the feedstock.

Alkyleneamines, such as non-cyclic polyalkylenepolyamines, find utility as dispersants, surfactants, chelants, catalysts, curing agents, extenders in polyurethanes, and as starting materials in the preparation of pesticides.

It is known that non-cyclic polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. The neutralization produces a waste stream of metal salt which must be disposed. Moreover, the process produces considerable amounts of cyclic products.

Certain patents teach the reforming of alkyleneamines, such as ethylenediamine, directly to non-cyclic polyalkylenepolyamines. For example, U.S. Pat. No. 4,316,841 discloses a process wherein ethylenediamine is reformed to higher molecular weight non-cyclic homologues, such as diethylenetriamine. Diethylenetriamine, on the other hand, is taught to be reformed to a mixture of higher and lower molecular weight ethylenepolyamines. The catalyst for this process is boron phosphate, a phosphate of a Group IA or IIA metal, or a phosphate of zirconium, antimony, tin or iron. Typically, these catalysts are soluble in amines and water. Consequently, the catalysts leach into the reaction mixture causing catalyst losses and separation problems.

Likewise, U.S. Pat. No. 4,316,840 discloses a process for the reforming of alkylenepolyamines in the presence of a catalyst comprising a metal sulfate or nitrate wherein the metal is selected from the group consisting of Groups IA and IIA metals, as well as zinc, zirconium, antimony, iron and tin. Ethylenediamine is taught to be reformed into polyethylenepolyamines. Diethylenetriamine is taught to be reformed into higher and lower molecular weight ethylenepolyamines. Large amounts of cyclic products, such as piperazine, are simultaneously produced. Typically, these catalysts are also soluble in amines and water. Consequently, catalyst leaching and separation problems are also inherent in these processes.

U.S. Pat. No. 4,568,746 teaches a process of reforming ethylenediamine in the presence of a catalyst containing nickel, cobalt or rhodium. Likewise, U.S. Pat. No. 4,625,030 teaches a process of contacting ethylenediamine in the presence of hydrogen with a catalyst comprising nickel impregnated or coated together with iridium or platinum on a support of silica-alumina to produce predominantly diethylenetriamine. Disadvantageously, these processes are limited to a narrow, low molecular weight product liner such as diethylenetriamine, and do not produce valuable higher homologues. Moreover, processes like these which employ hydrogenation catalysts require an expensive noble metal and further require hydrogen.

U.S. Pat. No. 3,956,329 discloses the deammoniation or cracking of an alkyleneamine, such as diethylenetriamine, over a zeolite catalyst containing at least one cation selected from the alkali metals, the alkaline earth metals, zinc group elements, or hydrogen or ammonium cations. The predominant products are cyclics, such as, triethylenediamine and piperazine.

U.S. Pat. No. 4,547,591 discloses the preparation of predominantly linear polyethylenepolyamines by reforming ethyleneamines in the presence of a silica-alumina catalyst, optionally containing an acidic phosphorus cocatalyst. Large amounts of cyclic products, such as piperazines, are simultaneously produced.

In addition to the specific disadvantages noted hereinabove, the aforementioned processes of the prior art are inflexible and cannot be tailored to meet changing market demands. For example, suppliers may find that at one time the market demands non-cyclic polyalkylenepolyamines, while the demand at another time may be for cyclic products. Moreover, within the broad demand for non-cyclic or cyclic products, the market may demand large supplies of one particular product and small supplies of another product. For example, the market need for non-cyclic triethylenetetramines and tetraethylenepentamines may exceed the need for mixtures of higher molecular weight non-cyclic polyethylenepolyamines, or vice versa. Cyclics, such as aminoethylpiperazine, may be valuable, whereas piperazine may be less so. Individually, the processes of the prior art cannot handle such broad needs.

It would be desirable to have a process which employs an inexpensive catalyst which is capable of directly reforming an alkyleneamine feedstock to a more valuable alkyleneamine product or mixture thereof which is different from the feedstock. It would be more desirable if the catalyst is insoluble in amines and water so as to avoid catalyst losses and separation problems. It would be even more desirable if the process does not require hydrogen gas or an expensive noble metal. Finally, it would be most desirable if the process is flexible and could be controlled to produce high yields of non-cyclic alkylenepolyamines or cyclic products, as desired.

SUMMARY OF THE INVENTION

This invention is a process of reforming alkyleneamines. The process comprises contacting an alkyleneamine feedstock or a mixture of two or more of such feedstocks in the liquid phase with a catalyst under reaction conditions such that an alkyleneamine or mixture of alkyleneamines is produced which is different from the feedstock. The feedstock is required to be essentially free of any alcohol which is capable of aminating the feedstock. Moreover, the catalyst which is employed in the reforming process of this invention is selected from the group consisting of:

(a) Group VB metal oxides, (b) Group VB metal phosphates,
(c) Group IIA metal silicates, and
(d) tungsten oxides, with the proviso that the catalysts are essentially free of hydrogenation metals, and with the additional proviso that the Group IIA metal silicate and tungsten oxide catalysts are essentially free of aluminum.

Advantageously, the process of this invention is a direct reforming process which does not require additional reactants beyond the reactant alkyleneamine feedstock. Moreover, the process of this invention does not require a neutralization step and the disposal of a waste metal salt stream. In addition, the catalysts of this process are insoluble in water and amines, therefore catalyst losses are minimized, and the separation of products from the catalyst is relatively easy. Even more advantageously, the catalysts are inexpensive when compared with the noble metal catalysts of the prior art. Most advantageously, the process of this invention can be controlled under certain conditions to give a high selectivity to non-cyclic alkyleneamines or alternatively cyclic products, as desired.

The alkyleneamine products of this invention are useful as dispersants, surfactants, curing agents, chelants, and catalysts and are also useful in the formation of urethane polymers, ureas, and pesticides.

DETAILED DESCRIPTION OF THE INVENTION

The feedstock alkyleneamine which is employed in the process of this invention comprises any alkylene or polyalkylene moiety containing at least two primary or secondary amine functionalities. The alkylene component can be straight or branched, substituted or unsubstituted. If substituted, the substituent should be inert. For the purposes of this invention the term "inert" means that the substituent does not inhibit or materially alter the reforming process of this invention. Such inert substituents include alkyl moieties, aryl moieties and also amino moieties. Preferably, the inert substituent is a $C_1$–$C_{12}$ alkyl moiety, such as methyl, ethyl, propyl, or butyl; or phenyl or substituted phenyl, such as tolyl or xylyl. Mixtures of the above-identified alkyleneamine feedstocks are also suitable.

Several examples of suitable alkyleneamines include ethylenediamine, propylenediamine, diethylenetriamine, linear and branched triethylenetetramines, linear and branched tetraethylenepentamines, and analogous higher homologues of polyethylenepolyamine and polypropylenepolyamine up to about twelve amine moieties as well as polyether alkyleneamines such as 2-($\beta$-aminoethoxy)aminoethane, 1,4-bis($\beta$-aminoethoxy)butane, and 1,4-bis($\gamma$-aminopropoxy)butane. Mixtures of any of the aforementioned compounds are also acceptable. Dow E-100 ® brand polyethylenepolyamine can also be employed in the process. Dow E-100 ® brand polyethylenepolyamine is a mixture comprising predominantly linear and branched pentaethylenehexamines, hexaethyleneheptamines, heptaethyleneoctamines, octaethylenenonamines, and optionally lesser amounts of nonaethylenedecamines and polyethylenepolyamines of a molecular weight equal to or lower than tetraethylenepentamine. While the above-identified alkyleneamines are representative of those which can be employed in the process of this invention, other alkyleneamines can be found which are equally suitable.

When a lower molecular weight alkyleneamine, such as ethylenediamine or diethylenetriamine, is employed as the feedstock, usually it reacts with itself to build a product mixture containing higher molecular weight polyalkylenepolyamines. In such instances, the preferred feedstock materials can be represented by the general formula:

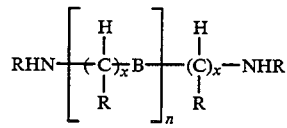

wherein each B is independently NR or O; each R is independently hydrogen, a $C_1$–$C_{12}$ alkyl moiety such as methyl, ethyl, or propyl, a $C_1$–$C_{12}$ aminoalkyl moiety, phenyl or an alkyl-substituted phenyl, such as tolyl or xylyl, and wherein when R is attached to an alkylene group, R can also be an amino ($NH_2$) moiety; each x is independently a number from 1 to about 12; and n is a number from 0 to 3. Preferably, each B is NR. More preferably, each B is NR and each R is hydrogen. Even more preferably, each B is NR, each R is hydrogen, x is 2, and the lower molecular weight alkyleneamine is ethylenediamine, diethylenetriamine, triethylenetetramine, or a mixture thereof. Most preferably, the lower molecular weight alkyleneamine is ethylenediamine.

When a high molecular weight alkyleneamine, such as the above-identified Dow E-100 ® brand polyethylenepolyamine, is employed as the feedstock, usually it is cracked to form a product mixture containing lower molecular weight alkyleneamines. In such instances, the preferred linear starting materials can be represented by the above-identified general formula with the exception that n is at least 4, and preferably from about 5 to about 150. High molecular weight materials, however, almost always contain many branched isomers which are suitable for the process of this invention, but which are not amenable to a preferred structure.

It is not intended that the reaction mixture in the process of this invention contain alcohols capable of reacting with the alkyleneamine feedstock or products. Reactions between alcohols and alkyleneamines are known in the prior art. Generally, such reactions yield polyalkylenepolyamines having a molecular weight higher than either the starting alcohol or starting amine. An example of such a process is the reaction of monoethanolamine with ethylenediamine to yield a mixture of diethylenetriamine, triethylenetetramine and higher homologues. The reforming process of this invention is not intended to embrace such alcohol-amine condensation reactions; therefore, alcohols with such a reactive capability should be excluded from the process of this invention.

Although it is preferred to carry out the reforming process of this invention in the absence of solvent, it is within the scope of the invention for a solvent to be used, if desired. Any solvent is acceptable provided that (1) it is not reactive with the alkyleneamine reactants or products, and (2) it does not decompose under the process conditions. Some examples of suitable solvents include saturated aliphatic hydrocarbons such as pentane, hexane, octane, nonane, and decane, and monocyclic aromatic hydrocarbons, such as benzene, toluene, and xylene. If necessary, water can be employed as a solvent, although it is not preferred. The amount of solvent employed in the reaction depends on the particular reactants and reaction conditions. Any amount of solvent is acceptable that meets the intended purpose of use. Typically, the solvent constitutes from about 5 weight percent to about 95 weight percent of the feed stream. Preferably, the solvent constitutes from about 10 weight percent to about 80 weight percent of the feed stream.

Optionally, the reforming process of this invention can be conducted in the presence of ammonia. The concentration of ammonia may be any operable concentration, but generally ranges from about 1 to about 20 moles of ammonia per mole of amine moieties present in the reactant. Preferably, the concentration of ammonia ranges from about 8 to about 10 moles of ammonia per mole of amine moieties present in the reactant.

Four kinds of catalysts can be employed in the reforming process of this invention including (a) Group VB metal oxides, (b) Group VB metal phosphates, (c) Group IIA metal silicates, and (d) tungsten oxides. These catalysts can be employed singly or in combination. A detailed description of each catalyst group is given hereinafter.

In accordance with the process of this invention, it is required that the above-identified catalysts be essentially free of hydrogenation metals. The phrase "essentially free of hydrogenation metals" means that the concentration of a hydrogenation metal in the catalyst must be less than about 0.5 weight percent, preferably, less than about 0.1 weight percent. For the purposes of this invention, a "hydrogenation metal" is identified as a metal which is capable of catalyzing the reductive reformation of reactant alkyleneamines to product alkyleneamines different from the starting material. An example of such a reaction is the reformation of ethylenediamine in the presence of hydrogen and a copper oxide catalyst to diethylenetriamine and triethylenediamine. The hydrogenation metals are known in the prior art to include the zerovalent metals of Group VIII, namely iron, cobalt, nickel, ruthenium, rhodium, palladium, osmium, iridium, and platinum; as well as zerovalent copper, chromium, molybdenum and the like, as disclosed in U.S. Pat. No. 4,625,030 and U.S. Pat. No. 4,568,746. Frequently, these metals are provided in the reductive reformation catalyst as the oxides, which are thereafter reduced to zerovalent metal by hydrogen.

A. Group VB Metal Oxides

Group VB metal oxides are suitably employed as catalysts in the reforming process of this invention. The Group VB elements include vanadium (V), niobium (Nb), and tantalum (Ta). Examples of suitable Group VB metal oxides include vanadium oxides such as VO, $VO_2$, $V_2O_3$, $V_2O_5$, $V_3O_5$, $V_5O_9$, $V_6O_{13}$; niobium oxides such as NbO, $NbO_2$, $Nb_2O_5$; tantalum oxides such as $Ta_2O_5$, as well as hydrated oxides including vanadates such as $H_3VO_4$, niobic acids such as $Nb_2O_4 \cdot xH_2O$, $H_8Nb_6O_{19} \cdot xH_2O$, and $[H_2Nb_6O_{16}]_m$, tantalic acid, as well as mixtures of Group VB metal oxides and/or hydrated metal oxides. Non-stoichiometric oxides are also suitable. Preferably, the Group VB metal is in the +3 or +5 oxidation state. More preferably, the Group VB metal oxide is an oxide or hydrated oxide of niobium. Most preferably, the Group VB metal oxide is a hydrated niobium oxide.

Generally, the common Group VB metal oxides are commercially available, while the less common oxides can be prepared by methods known in the art. The preparation of some less common Group VB metal oxides can be found in *Comprehensive Inorganic Chemistry*, Vols. 1–5, J. C. Bailar, Jr., H. J. Emeleus, R. Nyholm, and A. F. Trotman-Dickenson, eds., Pergamon Press, Oxford (1973), pp. 510–524 and 592–599.

B. Group VB Metal Phosphates

A Group VB metal phosphate can be suitably employed as a catalyst in the reforming process of this invention. As noted hereinbefore, the Group VB metals include vanadium, niobium, and tantalum. Examples of suitable Group VB metal phosphate compounds include. vanadium phosphates such as $V_2O_5 \cdot P_2O_5$ niobium phosphates such as $2Nb_2O_5 \cdot P_2O_5 \cdot 6H_2O$, $2Nb_2O_5 \cdot P_2O_5$, $NbOpO_4$, $Pnb_9O_{25}$; and tantalum phosphates such as $2Ta_2O_5 \cdot P_2O_5$, $2Ta_2O_5 \cdot P_2O_5 6H_2O$, $TaOPO_4$. Group VB metal meta-phosphates, fluorophosphates, hydrated phosphates, and non-stoichiometric phosphate compounds are also suitable, as are Group VB metal hydrogen phosphates. Preferably, the Group VB metal phosphate possesses a P/metal mole ratio no greater than about 3.0, more preferably, no greater than about 1.3. Most preferably, the Group VB metal phosphate possesses a P/metal mole ratio in the range from about 0.02 to about 1.0. Preferably, the Group VB metal phosphate is a niobium phosphate, more preferably, $NbOPO_4$ or the hydrated forms of $NbOPO_4$.

The Group VB metal phosphates are relatively easy to prepare. The preparations are described in *Comprehensive Inorganic Chemistry*, op. cit., pp. 612–613, and references cited therein. Preferably, the Group VB metal phosphate catalyst is prepared by reacting a catalyst precursor compound containing a Group VB metal with a phosphorus-containing compound, such as phosphoric acid, under conditions sufficient to generate the Group VB metal phosphate. Typical catalyst precursor compounds which can be employed as starting materials include Group VB metal oxides, hydrated oxides, halides, alkoxides, and carboxylic acid salts. Anhydrous or aqueous phosphoric acid can be employed, as can fluorinated phosphoric acids or fluorinated phosphorus-containing compounds. The phosphoric acid is typically employed as an 85 weight percent aqueous solution, however, additional water can be used to obtain Group VB metal phosphate compounds having higher surface area. More specifically, the catalyst precursor, such as a Group VB metal oxide, is heated with phosphoric acid at about atmospheric pressure and at a temperature in the range from about 130° C. to about 200° C. The weight ratio of phosphoric acid to precursor compound is preferably in the range from about 5 to about 20, more preferably, in the range from about 7 to about 15, most preferably, about 10. The length of time the precursor compound and phosphoric acid are heated varies depending upon the quantity of precursor compound employed and quantity of by-products which are driven off during heating. Typically, however, the mixture is heated for about one to two hours, however longer times may be employed. After heating, the mixture which comprises a liquid phase and a solid phase is cooled. The liquid is decanted from the solid, and the solid is washed with water and filtered. The washing and filtering may be repeated several times to ensure the removal of excess acid and unwanted ions. The filtered solid is dried at a temperature in the range from about 80° C. to about 150° C. in air for a time in the range from about 2 hours to about 50 hours to yield the Group VB metal phosphate. Typically, the metal phosphate compound is heat treated or calcined prior to use.

Preferably, the calcination is conducted at a temperature in the range from about 200° C. to about 500° C. for a time in the range from about 2 hours to about 50 hours.

C. Group IIA Metal Silicates

In accordance with the process of this invention, the reforming reaction can be conducted in the presence of a catalyst comprising a Group IIA metal silicate. Preferably, the metal of the metal silicate is magnesium, calcium, strontium, or barium. More preferably, the metal of the metal silicate is magnesium. The metal silicate can be employed in an amorphous form containing a distribution of silicate anions of various sizes. Alternatively, the metal silicate can be employed in a crystalline form, such as the siliceous zeolite structure exhibited by sodium magnesium silicate.

It is required that the metal silicate catalyst employed in the process of this invention be essentially free of aluminum. The phrase "essentially free of aluminum" means that the metal silicate contains less than about 5 weight percent aluminum. Preferably, the metal silicate contains less than about 2 weight percent aluminum, more preferably, less than about 1 weight percent aluminum.

The mole ratio of silicon to metal will vary in the metal silicate depending upon the metal cation, its valence, and the form of the silicate anion. For instance, in the case of magnesium silicate, the preferred silicon to magnesium mole ratio varies from about 0.5 to about 20. More preferably, the silicon to magnesium mole ratio varies from about 1 to about 10, most preferably, from about 1 to about 5. Other metal silicates may exhibit silicon to metal mole ratios which are different from the preferred ratios shown here for magnesium silicate.

The common Group IIA metal silicates which are employed in the process of this invention are commercially available. The less common silicates may be prepared by methods reported in *The Colloid Chemistry of Silica and Silicates* by Ralph K. Iler, Cornell University Press, 1955; or in *The Chemistry of Silica: Solubility, Polymerization, Colloid and Surface Properties, and Biochemistry* by Ralph K. Iler, John Wiley & Sons, 1979; and references therein.

The metal silicate catalyst can be prepared by a variety of synthetic methods. One, for example, requires the formation of a mixture of silica ($SiO_2$) with the oxide of the desired metal. The oxide mixture is calcined at a temperature sufficient to form the desired metal silicate. Another method, for example, depends upon the hydrolysis of mixtures of tetra(ethoxy)silicon and an alkoxide of the desired metal, e.g., magnesium dimethoxide. The hydrolysis reaction yields the desired metal silicate. Preferably, however, the metal silicates are prepared by direct precipitation from a mixture of two aqueous solutions. One of these solutions contains a soluble silicate salt, such as sodium silicate. Typically, the soluble silicate salt is dissolved in a minimum amount of water. Typically, the solution is heated, preferably to boiling, to aid in the dissolution of the salt. Optionally, the aqueous silicate solution can be acidified with strong acid, such as nitric acid, in order to prepare larger silicate anions, such as $Si_2O_5^{2-}$ or $Si_3O_7^{2-}$. Similarly, a soluble Group IIA metal compound containing the desired metal ion is dissolved in a minimum amount of water to make a second solution. The soluble metal compound can be, for example, a metal nitrate, such as magnesium nitrate, calcium nitrate, or barium nitrate: a metal chloride, such as magnesium chloride, or the like. Likewise, the second solution is heated to boiling to facilitate dissolution of the soluble metal compound. The two solutions are mixed and a precipitate forms of the desired metal silicate catalyst. The catalyst is filtered and dried by known methods.

D. Tungsten Oxides

Tungsten oxides are also suitably employed as catalysts in the reforming process of this invention. Suitable tungsten oxides comprise any binary compound of tungsten and oxygen. The term "binary compound" is given the usual definition of a chemical compound comprised of two elements, in this case tungsten and oxygen, for example $WO_2$ and $WO_3$. Salts of binary oxides are also suitable, such as $(NH_4)_2WO_4$.

The above-identified tungsten oxides can be simple mononuclear tungsten oxides, which are compounds containing only one tungsten atom, such as $(NH_4)_2WO_4$. Alternatively, the tungsten oxides can be multinuclear tungsten clusters, which are compounds containing a plurality of tungsten atoms, such as $(NH_4)_{10}(W_{12}O_{41})$. In addition, it is preferred that the tungsten be in the +4, +5, or +6 oxidation state. Examples of suitable tungsten oxides include $WO_2$, $WO_3$, $(NH_4)_2WO_4$, para-ammonium tungstate represented by $(NH_4)_{10}(W_{12}O_{41})$, as well as $H_2(W_6O_{19})$, $[(n-C_4H_9)_4N]_2(W_6O_{19})$, $(NR_4)_2(W_6O_{19})$ and $(NR_4)_4(W_{10}O_{32})$, wherein R is H or an alkyl moiety of up to about 20 carbon atoms; however, the tungsten oxides are not limited to only the aforementioned examples. The preferred mononuclear tungsten oxide is $(NH_4)_2WO_4$.

Also suitable for the process of this invention are multinuclear tungsten oxide clusters, or salts thereof, wherein a portion of the tungsten atoms is replaced by vanadium, niobium or tantalum. The preferred multinuclear tungsten oxide compounds can be represented by the general formula:

$$C_{2+w}[M_wW_{6-w}O_{19}]$$

wherein C is a monovalent cation, such as $Na^+$, $K^+$, $H^+$, or a quaternary ammonium salt ($NR_4^+$), wherein R is H or an alkyl moiety of up to 20 carbon atoms, such as butyl or propyl, w is an integer from 0 to 3, and M is vanadium (V), niobium (Nb), or tantalum (Ta). Preferably, C is tetrabutylammonium(+1).

It is required that the tungsten oxide catalyst employed in the process of this invention be essentially free of aluminum. The phrase "essentially free of aluminum" means that the tungsten oxide contains less than about 5 weight percent aluminum. Preferably, the tungsten oxide catalyst contains less than about 2 weight percent aluminum, more preferably, less than about 1 weight percent aluminum.

The more common of the tungsten oxides, such as $WO_2$, $WO_3$, $(NH_4)_2WO_4$, and para-ammonium tungstate can be purchased commercially from Alfa Products or Aldrich. The less common oxides and cluster compounds can be prepared by methods described in *Comprehensive Inorganic Chemistry*, Vol. 3, J. C. Bailar, Jr., H. J. Emeleus, R. Nyholm, and A. F. Trotman-Dickenson, eds., Pergamon Press Ltd.. Oxford (1973) pp. 763–769, and in "Isopolytungstates," by D. L. Kepert in *Progress in Inorganic Chemistry*, Vols. 4, Intersciences Press, New York (1962) p. 199. The preparation of $[(n-C_4H_9)_4N]_2(W_6O_{19})$ and various polyoxometalates is reported by M. Filowitz, R. K. C. Ho, W. G. Klemperer, and W. Shum in *Inorganic Chemistry*, 18, no. 1, 93–103 (1979), and by V. W. Day, W. G. Klemperer, and C. Schwartz in the *Journal of the American Chemical Society*, 109, No. 20, 6030–6044 (1987).

It is preferred that the aforementioned catalysts (A–D) be insoluble in the reforming reaction mixture, thereby acting as heterogeneous catalysts. Optionally, any of the catalysts can be made insoluble by (a) deposition onto a support material, or (b) binding with a refractory metal oxide or a support precursor. Any support or binder material is acceptable provided that it does not inhibit the reforming process of this invention. Suitable supports or binders include carbon and any refractory oxide such as silica, zirconia, thoria, magnesia, titania, kielselguhr, and mixtures of these materials. Alumina (hydrated and dehydrated forms) is also suitable, except as noted where the catalyst is required to be essentially free of aluminum. Suitable support precursors include hydrated metal oxides and metal alkoxides. Preferably, the support or binder material is silica or titania or alumina where allowed. The support material typically has a surface area of at least about 0.1 m$^2$/g. Preferably, the support material has a surface area in the range from about 5 m$^2$/g to about 600 m$^2$/g, most preferably in the range from about 50 m$^2$/g to about 200 m$^2$/g. These surface areas are measured by the Brunauer-Emmett-Teller (BET) method, as described by R. B. Anderson, in *Experimental Methods in Catalytic Research*, Academic Press (1968) pp. 48–66.

The catalyst can be deposited onto the support material in any known fashion, such as by impregnation or by precipitation in situ from the catalyst preparation reaction. In these types of preparation the catalyst is adsorbed onto the support. Alternatively, the catalyst can be chemically reacted onto the support. In this method a catalyst precursor compound is reacted with the hydroxyl functionalities of the support to yield a catalyst precursor chemically bound to the support. The bound catalyst precursor can then be converted by hydrolysis or heating into the supported catalyst. For example, niobium chloride may be reacted with the hydroxyl moieties of silica to yield niobium chloride bound through an oxygen to silicon. The bound niobium chloride can be heated to yield a bound niobium oxide catalyst.

The amount of catalyst which is employed in the process of this invention is any amount which is effective in catalyzing the reforming process and producing the desired alkyleneamine products. The amount of catalyst varies widely depending upon the specific reactants and process conditions employed. Typically, for a batch reaction the quantity of catalyst is in the range from about 0.1 weight percent to about 20 weight percent based on the weight of reactant alkyleneamine. Preferably, the amount of catalyst is in the range from about 1 weight percent to about 15 weight percent based on the weight of reactant alkyleneamine.

The process of this invention can be conducted in any suitable reactor, including batch reactors, continuous fixed-bed reactors, slurry reactors, fluidized bed reactors, and catalytic distillation reactors. When higher molecular weight products are desired, the reforming process is preferably conducted in the liquid phase in a continuous flow, fixed-bed reactor. When lower molecular weight products are desired, the reforming process, now a cracking process, is preferably conducted in a distillation reactor such that the feedstock is maintained in the liquid phase while the lighter products are continuously removed from the reaction mixture. This ensures that the reaction equilibrium is pushed towards lighter end-products.

The alkyleneamine feedstock or mixture thereof is contacted with the catalyst at any operable temperature which promotes the reforming process of this invention. Typically, the temperature is in the range from about 200° C. to about 400° C. Preferably, the temperature is in the range from about 250° C. to about 350° C. More preferably, the temperature is in the range from about 260° C. to about 315° C. Below the preferred lower temperature the conversion of reactant alkyleneamine may be low. Above the preferred upper temperature the selectivity for non-cyclic polyalkylene-polyamines may decrease.

Likewise, the alkyleneamine feedstock or mixture thereof is contacted with the catalyst at any operable pressure which promotes the reforming process of this invention. Typically, the pressure ranges from subatmospheric to about 4000 psig, but varies depending upon the reactor design, the feedstock and the types of products desired. For example, if a lower molecular weight alkyleneamine is being condensed to form a higher molecular weight polyalkylenepolyamine, then a fixed bed, continuous flow reactor is employed at a pressure sufficient to maintain the reactants in the liquid state. Under these circumstances the preferred pressure ranges from about 500 psig to about 3000 psig, most preferably, from about 1000 psig to about 2000 psig. Alternatively, if a higher molecular weight alkyleneamine is being cracked to form lower molecular weight products, then a distillation reactor is preferably employed with the feedstock in the liquid phase at a pressure ranging from subatmospheric to about atmospheric pressure. In batch reactors the pressure is autogenous, and depends upon the vapor pressures of the feedstock and products and upon the temperature of the reaction.

When the process of this invention is conducted in a continuous flow reactor, the flow rate of the reactants can be varied. Generally, the alkyleneamine or mixture thereof and any solvent are premixed to form a feed stream which is fed into the reactor at any operable flow rate which allows the reforming reaction to take place. Usually, the flow rate is expressed as the liquid hourly space velocity and is given in units of grams of total reactants per milliliter of total reactor volume per hour, g ml$^{-1}$ hr$^{-1}$. It is preferred to employ a liquid hourly space velocity in the range from about 0.1 g ml$^{-1}$ hr$^{-1}$ to about 10.0 g ml$^{-1}$ hr$^{-1}$, more preferably in the range from about 0.5 g ml$^{-1}$ hr$^{-1}$ to about 4.0 g ml$^{-1}$ hr$^{-1}$. It is understood that the hourly space velocity controls the residence time of the reactants in the continuous flow reactor.

When the process of this invention is conducted in a batch reactor, the reaction time determines the length of contact between the reactants and the catalyst. Any reaction time which yields the desired reformed products is acceptable. The reaction time depends upon the quantity of reactants, the quantity of catalyst, the temperature of the reaction and desired degree of conversion. Preferably, the reaction time in a batch reactor is in the range from about 1 hour to about 20 hours.

When the alkyleneamine feedstock or mixture of such feedstocks is contacted with at least one of the catalysts described hereinbefore, reforming occurs to yield an alkyleneamine or mixture of alkyleneamines which is different from the starting material or mixture. Characteristic of this difference, the molecular weight of the product alkyleneamine(s) is greater or less than the molecular weight of the alkyleneamine reactant. The variation in end-products depends upon the process conditions, the reactor design, the form of the catalyst, and the molecular weight of the reactants. When low molecular weight alkyleneamines are condensed to build higher molecular weight products, the products are predominantly linearly-extended (noncyclic) Polyalkylenepolyamines. Linearly-extended products comprise non-cyclic compounds of linear or branched structure. For example, ethylenediamine is reformed to build predominantly diethylenetriamine and linear and branched triethylenetetramines and tetraethylenepentamines. Alternatively, when high molecular weight alkyleneamines are cracked to lower molecular weight products, the products include significant amounts of both cyclic and non-cyclic materials. For example, Dow brand E-100 ® polyethylenepolyamine is typically cracked to lower molecular weight polyethylenepolyamines, such as triethylenetetramine and tetraethylenepentamine, and cracked to cyclics, such as piperazine and N-(2-aminoethyl)-piperazine. Alternatively, it is possible for higher molecular weight polyalkylenepolyamines to be reformed to build polymers rather than cracked to form lighter materials. Intermediate weight feedstocks, such as triethylenetetramines, usually give roughly equal mixtures of condensed and cracked products.

By-products of the process of this invention include ammonia and typically light weight alkylamines, such as ethylamine. Less desirable cyclic products containing new N-heterocycles, such as, 1,4-diaza-[2.2.2]-bicyclooctane may be formed in small amounts. Advantageously, the process of this invention essentially does not produce undesirable dehydrogenation products, such as, pyrazines.

The preferred linearly-extended polyalkylenepolyamine products can be represented by the general formula:

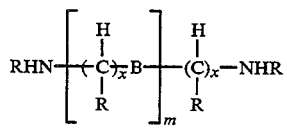

wherein each B is independently NR or O; each R is independently hydrogen, a $C_1$–$C_{12}$ alkyl moiety such as methyl, ethyl, or propyl, a $C_1$–$C_{12}$ aminoalkyl moiety, phenyl or an alkyl-substituted phenyl, such as tolyl or xylyl, and wherein when R is attached to an alkylene group, R can also De an amino ($NH_2$) moiety; each x is independently a number from 1 to about 12; and m is a positive number from 1 to about 300. Preferably, each B is NR. More preferably, each B is NR and each R is hydrogen. Even more preferably, each B is NR, each R is hydrogen, and x is 2. Most preferably, each B is NR, each R is hydrogen, x is 2, and m is 1, 2, or 3; and the polyalkylenepolyamines are diethylenetriamine, triethylenetetramine, and tetraethylenepentamine.

The preferred cracked products depend somewhat upon market demands. Currently, the preferred cracked products are non-cyclic polyalkylenepolyamines, such as triethylenetetramine and tetraethylenepentamine. In other economies cyclic products, such as piperazine and aminoethylpiperazine, may be the preferred cracked products.

For the purposes of this invention "conversion" is defined as the weight percentage of alkyleneamine feedstock lost as a result of reaction. The conversion varies widely depending upon the reactants, the form of the catalyst, and the process conditions, such as temperature, pressure, and flow rate. Within the preferred temperature ranger as the temperature increases the conversion generally increases. Within the preferred space velocity ranger as the space velocity increases the conversion generally decreases. Typically, the conversion of alkyleneamine is at least about 3 weight percent. Preferably, the conversion is at least about 10 weight percent; more preferably at least about 20 weight percent; even more preferably, at least about 30 weight percent; and most preferably, at least about 50 weight percent.

Likewise, for the purposes of this invention "selectivity" is defined as the weight percentage of converted alkyleneamine which forms a specific different alkyleneamine product. Typically, the selectivities also vary widely depending upon the reactants, the form of the catalyst, and the process conditions. For example, the process of this invention comprising the condensation of lower molecular weight alkyleneamines achieves high selectivities to linearly-extended polyalkylenepolyamines. Within the preferred temperature range as the temperature increases, the selectivity for linearly-extended polyalkylenepolyamines generally decreases. Within the preferred space velocity range as the space velocity increases, the selectivity for linearly-extended polyalkylenepolyamines generally increases. Preferably, the combined selectivity to all linearly-extended polyalkylenepolyamines is at least about 45 weight percent: more preferably, at least about 60 weight percent, even more preferably, at least about 75 weight percent, and most preferably, at least about 85 weight percent.

Where applicable, the efficiency of the reforming reaction in forming linearly-extended products can be measured by calculating the diethylenetriamine/piperazine weight ratio, abbreviated DETA/PIP. The higher the value of this ratio, the more linearly-extended polyalkylenepolyamines are present in the product mixture. Preferably, the DETA/PIP weight ratio is at least about 3. More preferably, the DETA/PIP weight ratio is at least about 10; most preferably, at least about 20.

Another measure of the efficiency of the reaction in forming linearly-extended products is the weight percentage of triethylenetetramines which are non-cyclic, % NC TETA. Preferably, % NC TETA is at least about 50 weight percent. More preferably, % NC TETA is at least about 70 weight percent, most preferably, at least about 90 weight percent. A third measure of the efficiency of the reaction in forming linearly-extended products is the weight percentage of tetraethylenepentamines which are non-cyclic, % NC TEPA. Preferably, % NC TEPA is at least about 50 weight percent. More preferably, % NC TEPA is at least about 70 weight percent, most preferably, at least about 90 weight percent.

The process of this invention comprising cracking of high molecular weight alkyleneamines, such as Dow-brand E-100 ® polyethylenepolyamines, to lower molecular weight alkyleneamines typically achieves selectivities to cyclic alkyleneamines of at least about 50 weight percent, however with reactive distillation the selectivities to non-cyclic alkyleneamines can be raised to at least about 70 weight percent.

In those instances where enrichment in cyclic products is desired, a commercial triethylenetetramine and/or tetraethylenepentamine feedstock, which contains some cyclic compounds, can be contacted with any of the above-identified catalysts in a distillation reactor to produce cyclics in high yield. Part of the feedstock is converted to lights, such as ethylenediamine and diethylenetriamine, which are distilled off. Part is converted to linearly-extended heavies, such as, pentaethylenehexamines and higher homologues. With time the reactor contents are enriched in heavies and cyclics, such as piperazine and aminoethylpiperazine. Selectivities to cyclics are preferably at least about 60 weight percent, 20 grams of material. The pressed pellets are dried at 120° C. for 5 hours, then heated slowly to a temperature of 400° C. and calcined thereat overnight to yield a boehmite-supported niobic acid catalyst. The calcined catalyst pellets are crushed and sieved to 14–20 mesh prior to use in the reactor.

(b) Reforming

The boehmite-supported niobic acid catalyst (20 g), prepared hereinabove, is loaded into a tubular, continuous flow, fixed-bed reactor. A feedstock comprising Dow brand E-100® polyethylenepolyamine is passed upward through the catalyst bed with the results shown in Rows 1a and 1b of Table I.

TABLE I

| Ex. | T °C. | P psig | Flow Rate ml/hr | Combined Selectivity[2] | | | Selectivity[3] | |
|-----|-------|--------|-----------------|-----|------|--------|--------|--------|
|     |       |        |                 | <<TEPA | TEPA | >>TEPA | TETA (% NC)[4] | TEPA (% NC)[4] |
| NR[1] | 25 | 0 | — | 1.2 | 12.5 | 86.4 | 0.9 (87.9) | 12.5 (58.4) |
| 1a | 280 | 700 | 40 | 24.1 | 17.2 | 58.7 | 10.8 (25.0) | 17.2 (29.2) |
| 1b | 300 | 700 | 60 | 43.6 | 15.5 | 40.9 | 14.8 (13.6) | 15.3 (10.6) |
| 2 | 300 | autogenous | — | 57.37 | 16.44 | 26.19 | 19.6 (14.0) | 16.0 (6.9) |

[1]"NR" means no reaction. Analysis of Dow E-100 ® brand polyethylenepolyamines is shown.
[2]"Combined selectivity" is weight percentage of converted feedstream as following combined products: <<TEPA contains EDA, PIP, DETA, AEEA, AEP, AEDETA, TETA, DIAEP, PEEDA and unidentified peaks. TEPA contains AETETA, BISPIP, TEPA, AEPEEDA, PEDETA and unidentified peaks. >>TEPA contains all cyclic and non-cyclic products higher than TEPAS.
[3]"Selectivity" is weight percentage of converted feedstream as identifiable TETA fraction (AEDETA, TETA, DIAEP and PEEDA) or TEPA fraction (AETETA, BISPIP, TEPA, AEPEEDA and PEDETA).
[4]"% NC" is weight percentage of TETA or TEPA which is non-cyclic.

more preferably, at least about 80 weight percent.

The following examples are illustrative of the invention, but are not intended to be limiting thereof. All percentages are given in weight percent, unless noted otherwise. In some instances the following abbreviations are used to indicate the reactants and products:

| EDA | ethylenediamine |
| AEEA | N-(2-aminoethyl)ethanolamine |
| DETA | diethylenetriamine |
| TETA | triethylenetetramine |
| TEPA | tetraethylenepentamine |
| PEHA | pentaethylenehexamine |
| PIP | piperazine |
| AEP | N-(2-aminoethyl)piperazine |
| AEDETA | N-(2-aminoethyl)diethylenetriamine |
| AETETA | N-(2-aminoethyl)triethylenetetramine |
| DIAEP | N,N'-bis(2-aminoethyl)piperazine |
| PEEDA | (piperazinylethyl)ethylenediamine |
| BISPIP | 1,2-bis(piperazinyl)ethane or bispiperazine |
| AEPEEDA | N-(aminoethylpiperazinylethyl)-ethylenediamine |
| PEDETA | (piperazinylethyl)diethylenetriamine |

EXAMPLE 1

Reforming of Dow Brand E-100 ® Polyethylenepolyamine (a) Preparation of Boehmite-Supported Niobic Acid Catalyst Boehmite or pseudoboehmite (60.0 g; Davison Alpha Alumina Monohydrate) and niobic acid, $Nb_2O_5 \times H_2O$ (60.0 g; Niobium Products Corp., CBMM number AD460) are mixed together, and the mixture is pressed at 20,000 psi into cylindrical pellets 1 inch in diameter by 1 inch in height. Each pellet contains approximately When Rows 1a and 1b of Table 1 are compared with the row labeled "NR", it is seen that a niobium oxide catalyst supported on boehmite alumina cracks Dow brand E-100 ® polyethylenepolyamines predominantly to polyethylenepolyamine products of molecular weight less than TEPA. It is also seen that the percentage of non-cyclics decreases on cracking, and that the majority of the cracked products from the continuous flow reactor is cyclic material.

EXAMPLE 2

(a) Preparation of Niobium Phosphate Catalyst

Niobic acid, $Nb_2O_5xH_2O$ (60.33 g; 0.211 mole) is stirred in 85 percent phosphoric acid (600 g; 5.22 moles) at 150° C. The niobium oxide dissolves to form a pink solution, and upon further heating a precipitate forms. The precipitate is boiled in the phosphoric acid solution for about 2 hours with stirring. The mixture is cooled to room temperature, and the liquid is decanted from the precipitate. Water (500 ml) is added to the precipitate with stirring, and the precipitate is filtered. The washing and filtering cycle is repeated five times. The filtered solid is dried at 110° C. under air for 2½ days to yield a niobium phosphate catalyst. The elemental analysis of the catalyst is consistent with the composition $NbOPO_4$.

(b) Cracking of Dow Brand E-100 ® Polyethylenepolyamines

The niobium phosphate catalyst (1 g) prepared hereinabove and Dow brand E-100 ® polyethylenepolyamine (50.1 g) are loaded into a stirred batch reactor. The reactor is purged with nitrogen, sealed and heated to 300° C. for 10 hr with the results shown in Row 2 of Table I. When Row 2 of Table I is compared with the row labeled "NR", it is seen that niobium phosphate catalyzes the cracking of higher molecular weight polyethylenepolyamines to lower molecular weight, predominantly cyclic polyethylenepolyamines.

EXAMPLE 3

Reforming of Ethylenediamine

Ethylenediamine (25 g, 0.42 mole) and the niobium phosphate catalyst (1.0 g) of Example 2 are loaded into a 300-cc glass-lined, stirred autoclave. The reactor is purged with nitrogen, heated to 300° C., and held at that temperature for nine hours. After cooling to room temperature the liquid products are analyzed by gas-liquid chromatography. A CAM (Carbowax amine deactivated) capillary column (15 m×0.25 mm dia.) is employed for the analysis of total amine products. Isomer distributions are determined on an SE-54 capillary column (30 m×0.25 mm dia.). The following results are obtained: conversion of EDA, 26 percent; selectivities on a feed-free basis to DETA, 58.3 percent, TETA, 11.4 percent; TEPA, 4.0 percent; PIP, 4.8 percent, and AEP, 3.7 percent. The DETA/PIP ratio is 12.1. The data show that niobium phosphate catalyzes the reforming of ethylenediamine to predominantly linearly-extended polyethylenepolyamines.

EXAMPLE 4

Reforming of Diethylenetriamine, Alone or in Mixture with Ethylenediamine

Niobic Acid, $Nb_2O_5 \cdot xH_2O$ (23.0 g, Niobium Products Corp., CBMM number AD 222) is pressed at 20,000 psi into cylindrical pellets 1 inch in diameter by 1 inch in length. Each pellet contains approximately 25 grams niobic acid. The pressed pellets are dried at 120° C. for 4 hours. The dried pellets are heated slowly under air to a temperature of 300° C. and calcined overnight at that temperature. The catalyst pellets are crushed and sieved to 14-20 mesh prior to use in the reactor. The sieved catalyst is packed into a fixed-bed reactor, and a feed comprising diethylenetriamine, alone or in mixture with ethylenediamine, is passed through the catalyst bed at a variety of reaction temperatures, pressures, and flow rates. The liquid products are analyzed by gas-liquid chromatography. A CAM (Carbowax amine deactivated) capillary column (15 m×0.25 mm dia.) is employed for the analysis of total amine products. Isomer distributions are determined on an SE-54 capillary column (30 m×0.25 mm dia.). The results are presented in Table II.

ethylenediamines to predominantly linearly-extended higher molecular weight polyethylenepolyamines. Moreovers below about 50 percent conversions the selectivity to non-cyclic tetraethylenepentamine is very high.

EXAMPLE 5

(a) Preparation of Silica-Supported Ammonium Tungstate

Para-ammonium tungstate (15.0 g; Amends Chemical Company) is added to 400 ml of water to which 5 ml of 30 percent hydrogen peroxide are added. The resulting mixture is heated with stirring at 80-90° C. for 60 minutes to form a solution. The solution is cooled to room temperature and added to a flask containing silica (25.0 g; Shell Silica Spheres S-980; 1.5 mm dia.). Water is removed from the silica mixture by rotary evaporation. The resulting solid is dried in a muffle furnace at 350° C. overnight to form a silica-supported tungsten oxide catalyst.

(b) Reforming of Diethylenetriamine

The supported tungsten oxide catalyst (7.9 g), prepared hereinabove, is used to reform diethylenetriamine according to the general procedure of Example 4. At a temperature of 315° C., a pressure of 1405 psig, and a flow rate of 1.0 g $ml^{-1} hr^{-1}$, the conversion of DETA is 20 percent and the selectivities are the following: EDA, 14 percent; TETA, 15 percent, TEPA, 52 percent, PEHA, 4 percent, PIP, 8 percent; AEP, 7 percent. The % NC TETA is 77 percent, and the % NC TEPA is 94 percent. The data show that silica-supported tungsten oxide catalyzes the reforming of diethylenetriamine to predominantly linearly-extended higher molecular weight polyethylenepolyamines.

EXAMPLE 6

(a) Preparation of Titania-Supported Ammonium Tungstate

Para-ammonium tungstate (30 g; Amends Chemical Co.) is added to 400 ml of water to which 10 cc of 30 percent hydrogen peroxide are added, and the resulting mixture is heated with stirring at 80-90° C. for 60 minutes to form a solution. The solution is cooled to room temperature and added to a flask containing titania (50 g; SAKI-CS200). Water is removed from the silica mixture by rotary evaporation. The resulting solid is dried in a muffle furnace at 350° C. overnight to form a titania-supported tungsten oxide catalyst.

TABLE II

| Ex. 4[1] | Temp (°C.) | P psig | LHSV g per ml-hr | % Conv. DETA | % Selectivity (feed-free basis)[2] | | | | |
|---|---|---|---|---|---|---|---|---|---|
| | | | | | EDA | TETA (% NC TETA)[3] | TEPA (% NC TEPA)[3] | PEHA | PIP | AEP |
| a | 280 | 1188 | 2.3 | 16 | — | 50 (99+) | 17 (99+) | 9 | 16 | 7 |
| b | 310 | 1188 | 2.3 | 37 | — | 42 (89) | 26 (89) | 4 | 18 | 9 |
| c | 285 | 1405 | 5.1 | 14 | 16 | 19 (84) | 43 (99+) | tr | 14 | 7 |
| d | 290 | 1253 | 1.4 | 47 | 16 | 21 (70) | 35 (93) | 5 | 16 | 7 |
| e | 315 | 1317 | 1.3 | 64 | 19 | 23 (59) | 30 (79) | 7 | 12 | 8 |

[1] Feedstream comprises (a-b) DETA and EDA in an EDA/DETA mole ratio of 2, and (c-e) DETA alone.
[2] % Selectivity is the weight percentage of specific product, based an the total weight of the product stream less the weight in the product stream of the feed component(s).
[3] (% NC TETA) and (% NC TEPA) are the weight percentages of triethylenetetramines and tetraethylenepentamines, respectively, which are non-cyclic.

It is seen that niobic acid catalyzes the reforming of diethylenetriamine, alone and in mixtures with (b) Reforming of Polyethylenepolyamines The supported tungsten oxide catalyst (1 g), prepared hereinabove, is loaded into an autoclave with Dow brand E-100 ® polyethylenepolyamines (65 ml). The analysis of E-100 ® is found at the row labeled "NR" in Table I. The autoclave is flushed with nitrogen, and sealed. Ammonia is added (30.8 g) and the temperature of the reactor is raised to 300° C. and maintained thereat for 10 hr. The pressure is autogenous at 2300 psig. After the reactor is cooled the contents are analyzed with the following results: Combined selectivities to <TEPA's, 36.13, TEPA's, 14.18, and >TEPA's, 49.69 weight percent. The selectivity to the identifiable products of the TETA fraction is 9.2 percent, of which 31.8 percent are non-cyclics. The selectivity to the identifiable products of the TEPA fraction is 11.6 percent, of which 22.8 percent are non-cyclics. It is seen that ammonium tungstate supported on titania catalyzes the cracking of high molecular weight polyethylenepolyamines predominantly to cyclic products of lower molecular weight.

EXAMPLE 7

(a) Preparation of Magnesium Silicate Catalyst

A first solution is prepared by dissolving $Na_2SiO_3 \cdot 9H_2O$ (180.0 g; 0.64 mole) in 1200 ml of water and heating to 80° C. Concentrated nitric acid (40.0 ml) is slowly added to the first solution, so that no precipitate forms during the addition. The solution is heated to boiling and the volume is raised to 2000 ml by the addition of water. A second solution is prepared by dissolving $Mg(NO_3)_2 \cdot 6H_2O$ (81.0 g; 0.32 mole) in 2000 ml of water. The second solution is heated to boiling, whereupon the first solution is added at a rate of 100 ml/min to the second solution with rapid stirring. A precipitate forms. The supernatant and the precipitate are heated and stirred for about 3 hours at boiling, then cooled to room temperature overnight. The precipitate is filtered, washed three times with 2000 ml of water, and refiltered. The filtercake is dried at 100° C. to yield a magnesium silicate catalyst.

(b-c) Reforming of Diethylenetriamine

The magnesium silicate catalyst (25.0 g; 8–20 mesh), prepared hereinabove, is calcined at (b) 300° C. or (c) 550° C. overnight, and then loaded into a fixed-bed continuous flow reactor. A feedstream comprising DETA is passed over the catalyst at a variety of process conditions with the results shown in Table III.

TABLE III

| | | | | | % Selectivity (DETA-free basis)[1] | | | | | |
|---|---|---|---|---|---|---|---|---|---|---|
| Ex. | Temp (°C.) | P psig | LHSV g ml$^{-1}$ hr$^{-1}$ | % DETA Conv. | EDA | TETA (% NC TETA)[2] | TEPA (% NC TEPA)[2] | PEHA | PIP | AEP |
| 7b | 262 | 1182 | 1.3 | 11 | 5 | 14 (53) | 64 (89) | — | 12 | 5 |
| 7b | 280 | 1393 | 3.6 | 19 | 6 | 17 (62) | 51 (97) | 10 | 10 | 6 |
| 7c | 280 | 1399 | 1.2 | 29 | 5 | 15 (51) | 53 (93) | 12 | 11 | 4 |
| 7c | 280 | 1405 | 4.0 | 12 | 6 | 14 (60) | 63 (95) | 1 | 11 | 5 |
| 7c | 300 | 1405 | 3.9 | 29 | 6 | 16 (49) | 51 (89) | 13 | 10 | 5 |

[1] % Selectivity is the weight percentage of specific product, based on the total weight of the product stream less the weight of DETA in the product stream.
[2] (% NC TETA) and (% NC TEPA) represent the weight percentage of triethylenetetramines and tetraethylenepentamines, respectively, which are non-cyclic.

It is seen that magnesium silicate catalyzes the reforming of diethylenetriamine to predominantly linearly-extended higher polyethylenepolyamines.

EXAMPLE 8

Reforming of a Mixture of Diethylenetriamine and Ethylenediamine

The magnesium silicate catalyst of Example 7(a) (14.3 g; 8-0 mesh) is calcined at (a) 300° C. or (b) 550° C. overnight. The calcined catalyst is loaded into a fixed-bed continuous flow reactor, and a mixture of diethylenetriamine and ethylenediamine in an EDA/DETA mole ratio of 2:1 is passed over the catalyst at a temperature of 280° C. and at the other process conditions shown in Table IV.

TABLE IV

| | | | | % Selectivity (EDA-DETA-free basis)[1] | | | | |
|---|---|---|---|---|---|---|---|---|
| Ex. | Pres psig | LHSV g ml$^{-1}$ hr$^{-1}$ | % DETA Conv. | TETA (% NC TETA)[2] | TEPA (% NC TEPA)[2] | PEHA | PIP | AEP |
| 8a | 1299 | 1.4 | 31 | 42 (82) | 32 (85) | 4 | 14 | 5 |
| 8b | 948 | 1.5 | 43 | 36 (73) | 33 (75) | 11 | 12 | 8 |
| 8b | 1200 | 4.0 | 9 | 44 (90) | 32 (99) | tr | 16 | 9 |

[1] % Selectivity is the weight percentage of specific product, based on the total weight of the product stream less the weight of EDA and DETA in the product stream.
[2] (% NC TETA) and (% NC TEPA) represent the percentage of triethylenetetramines and tetraethylenepentamines, respectively, which are non-cyclic.

The results in Table IV show that magnesium silicate catalyzes the reforming of mixtures of diethylenetriamine and ethylenediamine to predominantly linearly-extended higher molecular weight polyethylenepolyamines.

EXAMPLE 9

Reforming of Ethylenediamine

The magnesium silicate catalyst of Example 7(a) (14.3 g; 80–20 mesh) is calcined at 550° C. overnight and then loaded into the reactor of Example 8. Ethylenediamine is passed over the catalyst at a LHSV of 1.4 g ml$^{-1}$ hr$^{-1}$, a temperature of 300° C., and a pressure of 112 psig with the following results: EDA conversion, 31 percent; selectivity (on an EDA-free basis) to DETA, 53 percent; TETA, 23 percent; TEPA, 11 percent; PEHA, 1 percent, PIP, 7 percent; and AEP, 5 percent. The DETA/PIP ratio is 7.6. The % NC TETA is 79 percent, and the % NC TEPA is 67 percent. Thus, magnesium silicate catalyzes the reforming of ethylenediamine to predominantly linearly-extended higher molecular weight polyalkylenepolyamines.

EXAMPLE 10

Reforming of Polyethylenepolyamines

The magnesium silicate catalyst (1.0 g) of Example 7(a) and Dow Chemical Company E-100® brand polyethylenepolyamines (65 ml) are loaded into a 300 ml stainless steel autoclave with stirring of roughly 1500 rpm. The reactor is purged with nitrogen after which liquid ammonia (27.2 g) is added. The reactor is then sealed and heated to 300° C. and held at that temperature for 10 hr. During heating, the pressure is autogenous at 1900 psig. After cooling and venting, the product mixture is analyzed by gas phase chromatography with the results shown in Row 10 of Table V.

The reactor is sealed and purged with nitrogen. No ammonia is added. The reactor is heated to 300° C. and held thereat for 10 hr. During heating, the pressure is autogenous at 200 psig. After cooling and venting, the product mixture is analyzed by gas phase chromatography with the results shown in Row 11 of Table V. When Row 11 is compared with Row "NR" in Table V, it is seen that magnesium trisilicate catalyzes the cracking of high molecular weight polyethylenepolyamines to lower molecular weight polyethylenepolyamines of predominantly cyclic homologues.

EXAMPLE 12

Reforming of Polyethylenepolyamines

The magnesium silicate catalyst of Example 7(a) (1 g) and Dow brand E-100® polyethylenepolyamines (80 ml) are loaded into a distillation reactor. The reactor is heated to about 300° C. at atmospheric pressure. The distillates (10 ml) are collected over an 18 hr period and analyzed with the results shown in Row 12a of Table V. When Row 12a is compared with Row "NR" in Table V, it is seen that the distillates essentially comprise ethyleneamines of molecular weight lower than that of TEPA. Specifically, the distillate fraction contains EDA (42.85), PIP (11.61), DETA (14.66), AEP (4.42) and TETA (2.0). Likewise, the bottoms are analyzed with the results shown in Row 12b of Table V. When Row 12b is compared with Row "NR" of Table V, it is seen that the bottoms comprise polyethylenepolyamines predominantly of higher molecular weight than TEPA.

EXAMPLE 13

Reforming of Tetraethylenepentamines (TEPA)

The magnesium silicate catalyst (2.0 g) of Example 11 and a commercial sample of TEPA (140.7; Dow Chemical Co.) are loaded into a distillation reactor. The temperature is maintained at 300° C. and the lights are distilled over at atmospheric pressure and collected. The analysis of the collected lights (weight percent by GC) is as follows: 18.9 EDA, 8.71 PIP, 14.4 DETA, 17.75 AEP, 0.74 TETA, 1.98 DIAEP, 1.18 PEEDA, and 0.49 AEPEEDA. The combined results are shown in Row 13 of Table VI.

TABLE V

| Ex. | T °C. | P psig | Time hr | Combined Selectivity[2] | | | Selectivity[3] | |
|---|---|---|---|---|---|---|---|---|
| | | | | <<TEPA | TEPA | >>TEPA | TETA (% NC)[4] | TEPA (% NC)[4] |
| NR[1] | 25 | 0 | — | 1.2 | 12.5 | 86.4 | 0.9 (87.9) | 12.5 (58.4) |
| 10 | 300 | 1900 | 10 | 19.96 | 14.58 | 65.66 | 7.2 (47.4) | 13.9 (42.4) |
| 11 | 300 | 200 | 10 | 35.55 | 20.37 | 44.08 | 17.8 (35.4) | 20.4 (27.8) |
| 12a | 300 | 0 | 18 | 96.98 | 2.02 | 1.01 | 2.0 (64.4) | 1.0 (56.3) |
| 12b | 300 | 0 | 18 | 16.22 | 12.13 | 71.65 | 11.3 (44.2) | 16.6 (38.1) |
| 18 | 300 | 21 cm Hg | 10 | 78.79 | 15.85 | 5.39 | 15.2 (63.1) | 15.8 (60.6) |

[1]"NR" means no reaction. Analysis of DOW E-100 ® brand polyethylenepolyamines is shown.
[2]"Combined selectivity" is weight percentage of converted feedstream as following combined products: <<TEPA contains EDA, PIP, DETA, AEEA, AEP, AEDETA, TETA, DIAEP, PEEDA and unidentified peaks. TEPA contains AETETA, BISPIP, TEPA, AEPEEDA, PEDETA and unidentified peaks. >>TEPA contains all cyclic and non-cyclic products higher than TEPAS.
[3]"Selectivity" is weight percentage of converted feedstream as identifiable TETA fraction (AEDETA, TETA, DIAEP and PEEDA) or TEPA fraction (AETETA, BISPIP, TEPA, AEPEEDA and PEDETA).
[4]"% NC" is weight percentage of TETA or TEPA which is non-cyclic.

When Row 10 of Table V is compared with Row "NR", it is seen that high molecular weight polyethylenepolyamines are reformed via cracking in the presence of magnesium silicate to lower molecular weight polyethylenepolyamines of predominansly cyclic homologues.

EXAMPLE 11

Reforming of Polyethylenepolyamines

A commercial magnesium trisilicate [(MgO)$_2$(SiO$_2$)$_3$] (1.0 g, Mallinkrodt) and Dow Chemical Company E-100® brand polyethylenepolyamines (52.5 g) are loaded into a 300 ml stainless steel, stirred autoclave.

TABLE VI

| Ex. | T °C. | P psig | Time hr | Combined Selectivity[4] | | | Selectivity[3] | |
|---|---|---|---|---|---|---|---|---|
| | | | | <<TEPA | TEPA | >>TEPA | TETA (% NC)[5] | TEPA (% NC)[5] |
| NR[1] | 25 | 0 | — | 1.5 | 96.2 | 2.3 | 1.4 (41.1) | 96.1 (63.5) |
| 13 | 300 | 0 | 47.8 | 99.5 | 0.49 | 0 | 3.9 (18.9) | 0.5 (0.0) |
| NR[2] | 25 | 0 | — | 20.5 | 67.3 | 12.3 | 22.2 (60.7) | 65.4 (63.5) |
| 14 | 300 | 240 | 10 | 56.2 | 27.5 | 16.3 | 28.3 (32.5) | 27.2 (25.0) |
| 15 | 300 | 100 | 10 | 28.8 | 56.9 | 14.3 | 22.3 (54.2) | 55.9 (56.8) |

[1,2] NR means no reaction.
[1] Analysis of Dow brand TEPA is shown.
[2] Analysis of Aldrich brand TEPA is shown.
[3] "Combined selectivity" is weight percentage of converted feedstream as following combined products: <<TEPA contains EDA, PIP, DETA, AEEA, AEP, AEDETA, TETA, DIAEP, PEEDA and unidentified peaks. TEPA contains AETETA, BISPIP, TEPA, AEPEEDA, PEDETA and unidentified peaks. >>TEPA contains all cyclic and non-cyclic products higher than TEPAS.
[4] "Selectivity" is weight percentage of converted feedstream as identifiable TETA fraction (AEDETA, TETA, DIAEP and PEEDA) or TEPA fraction (AETETA, BISPIP, TEPA, AEPEEDA and PEDETA).
[5] "% NC" is weight percentage of TETA or TEPA which is non-cyclic.

When Row 13 is compared with Row "NR[1]" in Table VI, it is seen that magnesium silicate catalyzes the cracking of TEPA to lighter polyethylenepolyamines with nearly equal cyclic and non-cyclic homologues by weight.

EXAMPLE 14

Reforming of TEPA

The magnesium trisilicate (1 g; Mallinkrodt) of Example 11 and a commercial sample of TEPA (51 g; Aldrich Chemical Co.) are loaded into a 300 ml autoclave. The reactor is purged with nitrogen, sealed and heated to 300° C. for 10 hr with the results shown in Row 14 of Table VI. When Row 14 is compared with Row "NR[2]" in Table VI, it is seen that magnesium silicate catalyzes the reforming of TEPA to polyethylenepolyamines of predominantly lower molecular weight. Higher molecular weight materials are also formed in a selectivity increased by 4 percent. The products are predominantly cyclic materials.

EXAMPLE 15

Reforming of TEPA

The niobic acid catalyst supported on boehmite alumina (1 g) prepared in Example 1a and a commercial sample of TEPA (51 g; Aldrich Chemical Co.) are loaded into a 300 ml autoclave. The reactor is purged with nitrogen, sealed and heated to 300° C. for 10 hr with the results shown in Row 15 of Table VI. When Row 15 is compared with Row "NR[2]" of Table VI, it is seen that some cracking and condensation of the TEPA occurs to yield polyethylenepolyamines of both higher and lower molecular weighty with cracking products predominating over products having molecular weight increase. The new materials are predominantly cyclic.

EXAMPLE 16

Reforming of a Mixture of Polyethylenepolyamines and Ethylenediamine

The magnesium silicate catalyst (1.0 g) of Example 7(a), ethylenediamine (35 ml) and Dow brand E-100® polyethylenepolyamines (35 ml) are loaded into an autoclave which is thereafter sealed and flushed with gaseous nitrogen. The autoclave is heated at 300° C. for 10 hr. The pressure is autogenous at 580 psig. After cooling and venting the contents are analyzed with the results shown in Table VII.

TABLE VII

| Ex. | T °C. | P psig | Time hr | Combined Selectivity[2] | | | Selectivity[3] | |
|---|---|---|---|---|---|---|---|---|
| | | | | <<TEPA | TEPA | >>TEPA | TETA (% NC)[4] | TEPA (% NC)[4] |
| NR[1] | 25 | 0 | — | 29.34 | 8.79 | 61.63 | 0.2 (62.9) | 8.8 (58.7) |
| 16 | 300 | 580 | 10 | 58.10 | 12.49 | 29.41 | 10.1 (36.2) | 11.5 (26.5) |
| 17 | 300 | 385 | 10 | 67.01 | 9.52 | 23.47 | 10.4 (16.0) | 7.3 (2.0) |

[1] "NR" means no reaction. Analysis of a mixture of Dow E-100 ® brand polyethylenepolyamines and EDA is shown.
[2] "Combined selectivity" is weight percentage of converted feedstream as following combined products: <<TEPA contains EDA, PIP, DETA, AEEA, AEP, AEDETA, TETA, DIAEP, PEEDA and unidentified peaks. TEPA contains AETETA, BISPIP, TEPA, AEPEEDA, PEDETA and unidentified peaks. >>TEPA contains all cyclic and non-cyclic products higher than TEPAS.
[3] "Selectivity" is weight percentage of converted feedstream as identifiable TETA fraction (AEDETA, TETA, DIAEP and PEEDA) or TEPA fraction (AETETA, BISPIP, TEPA, AEPEEDA and PEDETA).
[4] "% NC" is weight percentage of TETA or TEPA which is non-cyclic.

When Row 16 is compared with Row "NR" in Table VII, it is seen that magnesium silicate catalyzes the reforming of mixtures of Dow brand E-100® polyethylenepolyamines and EDA to predominantly cyclic polyethylenepolyamines of molecular weight equal to TEPA or lower.

EXAMPLE 17

Reforming of a Mixture of Polyethylenepolyamines and Ethylenediamine

The niobium phosphate catalyst (1.0 g) of Example 2, ethylenediamine (35 ml) and Dow brand E-100 ® polyethylenepolyamines (35 ml) are loaded into an autoclaver which is thereafter sealed and flushed with gaseous nitrogen. The autoclave is heated at 300° C. for 10 hr. The pressure is autogenous at 385 psig. After cooling and venting the contents are analyzed with the results shown in Table VII. When Row 17 is compared with Row "NR" in Table VII, it is seen that niobium phosphate catalyzes the reforming of mixtures of Dow brand E-100 ® polyethylenepolyamines and EDA to predominantly cyclic polyethylenepolyamines of molecular weight equal to TEPA or lower.

EXAMPLE 18

Reforming of Polyethylenepolyamines

The magnesium silicate catalyst (2.0 g) of Example 11 and a commercial sample of polyethylenepolyamines (120.0 g, Dow Chemical Company E-100 ®) are loaded into a distillation reactor. The temperature is maintained at 300° C., and the lights are distilled over at a reduced pressure of 21 cm Hg and collected, while maintaining the 120 g in the distillation pot by continually adding E-100. The analysis of the lights (22.8 g) collected over a 10 hr period is as follows (weight percent by GC): 16.3 EDA, 3.56 PIP, 21.3 DETA, 9.09 AEP, 0.77 AEDETA, 8.79 TETA, 2.76 DIAEP, 2.84 PEEDA, 2.14 AETETA, 0.39 BISPIP, 7.47 TEPA, 4.13 AEPEEDA, and 1.72 PEDETA. The combined results are shown in Row 18 of Table V. The non-cyclics produced by cracking E-100 ® brand polyethylenepolyamines in the reduced pressure distillation reactor comprise 72 weight percent of the identified lights of molecular weight less than the TEPA's.

What is claimed is:

1. A process of reforming alkyleneamines to higher molecular weight polyalkylenepolyamines comprising contacting with a catalyst an alkyleneamine feedstock represented by the general formula:

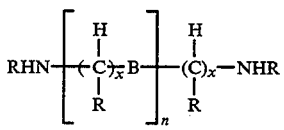

wherein each B is independently NR or O; each R is independently hydrogen, a $C_{1-12}$ alkyl moiety or $C_{1-12}$ aminoalkyl moiety, phenyl or alkyl-substituted phenyl, and wherein when R is bound to a carbon atom, R is also amino; each x is independently an integer from 1 to about 12; and n is an integer from 0 to 3, the feedstock being in the liquid phase and being essentially free of any alcohol which is capable of aminating the feedstock, the catalyst being selected from the group consisting of tungsten oxides, characterized as binary compounds of tungsten and oxygen or salts thereof or binary compounds of tungsten and oxygen wherein a portion of the tungsten atoms has been replaced by vanadium, niobium or tantalum, with the proviso that the tungsten oxide catalysts are essentially free of aluminum and essentially free of hydrogenation metals, the contacting occurring at a temperature in the range from about 250° C. to about 150° C. and under process conditions such that a mixture of polyalkylenepolyamines is formed predominantly of higher molecular weight than the feedstock and predominantly of non-cyclic homologues.

2. The process of claim 1 wherein each B is NR and each R is hydrogen.

3. The process of claim 2 wherein the alkyleneamine is ethylenediamine.

4. The process of claim 2 wherein the alkyleneamine is diethylenetriamine.

5. The process of claim 1 wherein the products are predominantly non-cyclic linearly-extended polyalkylenepolyamines represented by the general formula:

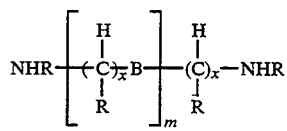

wherein each B is independently NR or O; each R is independently hydrogen, a $C_1$–$C_{12}$ alkyl moiety, a $C_1$–$C_{12}$ aminoalkyl moiety, phenyl or alkyl-substituted phenyl and wherein when R is attached to a carbon atom, R is also amino; each x is independently an integer from 1 to about 12; and m is an integer from 1 to about 300.

6. The process of claim 1 wherein the catalyst is tungsten oxide represented by the formula:

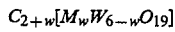

wherein C is a monovalent cation, M is vanadium (V), niobium (Nb) or tantalum (Ta), and w is an integer from 0 to 3.

7. The process of claim 1 wherein the catalyst is ammonium tungstate.

8. The process of claim 1 wherein the quantity of catalyst is in the range from about 0.1 weight percent to about 20 weight percent based on the weight of the alkyleneamine feedstock.

9. The process of claim 1 wherein the temperature is in the range from about 260° C. to about 315° C.

10. The process of claim 1 wherein the pressure is in the range from about subatmospheric to about 4000 psig.

11. The process of claim 1 wherein the liquid hourly space velocity is in the range from about 0.1 g ml$^{-1}$ hr$^{-1}$ to about 10.0 g ml$^{-1}$ hr$^{-1}$.

12. The process of claim 1 wherein ammonia is employed.

13. The process of claim 1 wherein the process is conducted in a fixed-bed continuous flow reactor.

14. The process of claim 1 wherein the process is conducted in a distillation reactor.

15. A process of cracking an alkyleneamine feedstock comprising contacting with a catalyst an alkyleneamine represented by the general formula:

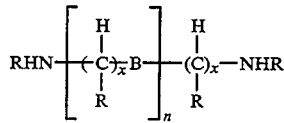

wherein each B is independently NR or O; each R is independently hydrogen, a $C_{1-12}$ alkyl moiety or $C_{1-12}$ aminoalkyl moiety, phenyl or alkyl-substituted phenyl, and wherein when R is bound to a carbon atom, R is also amino; each x is independently an integer from 1 to about 12; and n is an integer equal to or greater than 4, the feedstock being in the liquid phase and being essentially free of any alcohol which is capable of aminating the feedstock, the catalyst being selected from the group consisting of tungsten oxides, characterized as binary compounds of tungsten and oxygen or salts thereof or binary compounds of tungsten and oxygen wherein a portion of the tungsten atoms has been replaced by vanadium, niobium or tantalum, with the proviso that the tungsten oxide catalysts are essentially free of aluminum and essentially free of hydrogenation metals, the contacting occurring at a temperature in the range from about 250° C. to about 350° C. and under other process conditions such that a mixture of alkyleneamines is formed predominantly of lower molecular weight than the feedstock.

16. The process of claim 15 wherein the alkyleneamine is Dow E-100 ® brand polyethylenepolyamine.

17. The process of claim 15 wherein the products are cracking products.

18. The process of claim 15 wherein the catalyst is ammonium tungstate or a tungsten oxide represented by the general formula:

$$C_{2+w}[M_w W_{6-w} O_{19}]$$

wherein C is a monovalent cation, M is vanadium (V), niobium (Nb) or tantalum (Ta), and w is an integer from 0 to 3.

19. The process of claim 15 wherein the pressure is in the range from about subatmospheric to about 4000 psig, and if a flow reactor is employed, then the liquid hourly space velocity is in the range from about 0.1 g ml$^{-1}$ hr$^{-1}$ to about 10.0 g ml$^{-1}$ hr$^{-1}$.

20. The process of claim 15 wherein ammonia is employed.

21. The process of claim 15 wherein the reactor is a fixed-bed continuous flow reactor or a distillation reactor.

22. A process of cracking a feedstock of polyethylenepolyamines comprising contacting a feedstock of polyethylenepolyamines containing predominantly linear and branched pentaethylenehexamines, hexaethyleneheptamines, heptaethyleneoctamines, and octaethylenenonamines, and optionally containing ethylenediamine, the feedstock being in the liquid phase and being essentially free of any alcohol which is capable of aminating the feedstock, with a catalyst selected from the group consisting of tungsten oxides, characterized as binary compounds of tungsten and oxygen or salts thereof or binary compounds of tungsten and oxygen wherein a portion of the tungsten atoms has been replaced by vanadium, niobium or tantalum, with the proviso that the tungsten oxide catalysts are essentially free of aluminum and essentially free of hydrogenation metals, the contacting occurring in a distillation reactor at a temperature in the range from about 250° C. to about 350° C. and under other process conditions such that a mixture of polyethylenepolyamines is formed containing predominantly tetraethylenepentamines and ethylenepolyamines of molecular weight lower than tetraethylenepentamines.

23. The process of claim 22 wherein the polyethylenepolyamines feedstock is Dow E-100 ® brand polyethylenepolyamines.

24. A process of reforming ethylenediamine or diethylenetriamine comprising contacting ethylenediamine or diethylenetriamine, which is essentially free of any alcohol which is capable of aminating the ethylenediamine or diethylenetriamine, in the liquid phase with a catalytic amount of ammonium tungstate which is essentially free of aluminum and essentially free of hydrogenation metals, the contacting occurring at a temperature in the range from about 250° C. to about 350° C. such that a mixture of predominantly non-cyclic polyethylenepolyamines is formed.

* * * * *

UNITED STATES PATENT AND TRADEMARK OFFICE
CERTIFICATE OF CORRECTION

PATENT NO. : 5,410,087
DATED : Apr. 25, 1995
INVENTOR(S) : George E. Hartwell, et al It is certified that error appears in the above-indentified patent and that said Letters Patent is hereby corrected as shown below:

On the title page, item [21], "54,195" should read --154,195--.

Column 24, line 1, "150°C" should read --350°C--.

Signed and Sealed this

Twenty-third Day of July, 1996

Attest:

BRUCE LEHMAN

Attesting Officer        Commissioner of Patents and Trademarks